United States Patent [19]

Senet et al.

[11] Patent Number: 4,806,286

[45] Date of Patent: Feb. 21, 1989

[54] PROCESS FOR THE PREPARATION OF ACID CHLORIDES BY PHOSGENATION OF ACIDS, AND CATALYSTS FOR THIS PROCESS

[75] Inventors: Jean-Pierre Senet, La Chapelle La Reine; Patricia Gauthier, Cerny; Thierry Malfroot, Saintry Sur Seine; Patrick Wolf, Vert Le Petit, all of France

[73] Assignee: Societe Nationale des Poudres et Explosifs, Paris, France

[21] Appl. No.: 888,208

[22] Filed: Jul. 23, 1986

[30] Foreign Application Priority Data

Jul. 23, 1985 [FR] France .................. 85 11248

[51] Int. Cl.$^4$ ............................................ C07C 51/60
[52] U.S. Cl. .............................. 260/544 K; 260/544 Y; 502/150; 502/152; 502/167
[58] Field of Search ................... 260/544 K, 544 Y; 502/167

[56] References Cited

U.S. PATENT DOCUMENTS 3,149,155  9/1964  Seefelder et al. ............. 260/544 K
3,547,960 12/1970  Hauser ......................... 260/544 K
3,932,451  1/1976  Bigelow et al. ................ 560/161

*Primary Examiner*—Paul J. Killos
*Attorney, Agent, or Firm*—Burns, Doane, Swecker & Mathis

[57] ABSTRACT

The invention relates to a new process for the preparation of carboxylic acid chlorides by phosgenation of the corresponding carboxylic acid in the presence of a catalyst.

This process is characterized in that the said catalyst is chosen from the compounds represented by the formulae

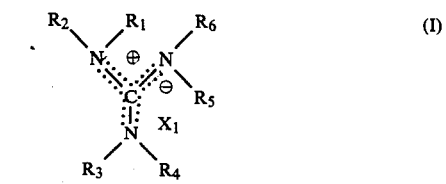

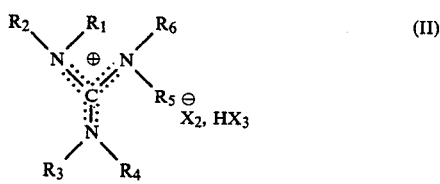

in which $R_1$ to $R_6$, which are identical of different, denote:

aliphatic, alicyclic, araliphatic or aromatic radicals, or form, in pairs, with the nitrogen atom to which they are attached or with the N-C-N group, a 5- or 6-membered heterocyclic ring.

The process applies to most carboxylic acids.

The acid chlorides obtained are known and used to produce radical polymerization initiators or pesticides.

13 Claims, No Drawings

PROCESS FOR THE PREPARATION OF ACID CHLORIDES BY PHOSGENATION OF ACIDS, AND CATALYSTS FOR THIS PROCESS

The invention relates to a new process for the preparation of carboxylic acid chlorides.

It is known to prepare carboxylic acid chlorides by phosgenation of the corresponding carboxylic acid. The reaction is as follows:

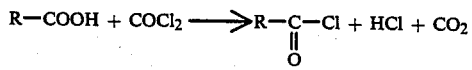

In the absence of a catalyst, however, the reaction takes place only at a high temperature (French Pat. No. 732,078) and, in some cases, at a high pressure of at least 10 atmospheres (U.S. Pat. No. 2,657,233).

Use of a catalyst is therefore essential if acid chlorides are to be obtained under economically acceptable conditions.

Powdered or, preferably, granulated activated charcoal is very frequently employed. Unfortunately, it is difficult to recycle, since it loses its activity, and a great number of very fine charcoal particles remain suspended in the acid chloride. Unsaturated or chlorinated secondary products may form, especially during the preparation of aliphatic acid chlorides, being due to the partial decomposition of phosgene into carbon monoxide and chlorine (French Pat. No. 839,231).

Other catalysts have also been proposed:
tertiary amines and their hydrochlorides (French Pats. Nos. 864,515 and 2,212,319),
quaternary ammonium and phosphonium salts, tertiary sulphonium salts (British Pat. No. 1,159,266),
amides (U.S. Pat. No. 3,149,155),
imidazoles and their derivatives (U.S. Pat. No. 3,547,960), pentasubstituted guanidines (Hungarian Pat. No. 160,740), and
tetrasubstituted ureas and phosphoramides (French Pat. No. 1,226,245).

However, all the processes which make use of these catalysts possess the following disadvantages in various degrees.

The catalyst quantity which is necessary is considerable and is in most cases more than 1 mole % based on the acid. As a result, the acid chloride has to be distilled in order to remove the catalyst residues from it. Now, this distillation is particularly difficult in the case of relatively nonvolatile acid chlorides.

The yields are variable and not always adequate. High inconvenient byproducts such as carbamyl chlorides and/or tarry residues are produced, and this makes it difficult to use the processes and to purify the acid chlorides.

It was consequently very important to find a new catalyst for the preparation of acid chlorides, that would make it possible to simplify the various operations, and to reduce the quantity of secondary products.

The subject of the present invention is a process for the preparation of acid chlorides by phosgenation of carboxylic acids in the presence of a new catalyst.

The catalyst according to the invention is chosen from the group of hexasubstituted guanidinium salts or of their complexes with acids containing hydrogen and a halogen, represented by the formulae:

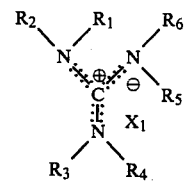

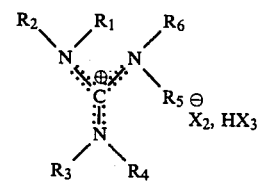

in which $R_1$, $R_2$, $R_3$, $R_4$, $R_5$ and $R_6$, which are identical or different, denote:

saturated or unsaturated, substituted or otherwise, linear or branched aliphatic radicals, no unsaturation being situated on the carbon adjoining the nitrogen atom, saturated or otherwise, substituted or otherwise, alicyclic radicals, no unsaturation being situated on the carbon adjoining the nitrogen atom, substituted or otherwise, araliphatic radicals, substituted or otherwise, aromatic radicals, or form, with the nitrogen atom to which they are attached and with the other radical attached to the same nitrogen atom, a saturated or otherwise, substituted or otherwise, heterocyclic ring, no unsaturation being situated on the carbon adjoining the nitrogen atom, or form, with the nitrogen atom to which they are attached, the central carbon, another nitrogen atom and a radical attached to this nitrogen atom, a saturated or otherwise, substituted or otherwise, heterocyclic ring, no unsaturation being situated on a carbon adjoining the nitrogen atoms, $x_1$ denotes an anion chosen from the group comprising $Cl^\ominus$, $Br^\ominus$, $I^\ominus$, $BF_4^\ominus$, $CN^\ominus$, $ClO_4^\ominus$, $NO_3^\ominus$, $NO_2^\ominus$, $OCN^\ominus$, $CH_3SO_4^\ominus$, $HSO_4^\ominus$ and $X_2$ and $X_3$, which are identical or different, denote chlorine or bromine atoms.

The cation in the above formulae can also be written in the following resonance forms:

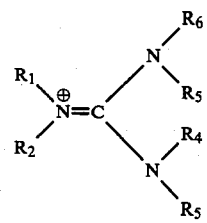
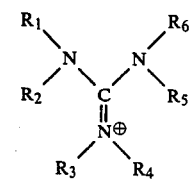

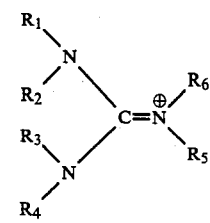

The catalysts of the present invention are of particular interest because it has been found that they also catalyse the decomposition of acid anhydrides which are formed as byproducts in the principal reaction.

Another advantage of the catalysts of the invention is that they can be employed in quantities which are much smaller than the quantities generally employed in the other processes.

These quantities are between $10^{-4}$ and $5 \times 10^{-3}$ equivalent per equivalent of acid and preferably between $10^{-4}$ and $10^{-3}$ equivalent.

A greater quantity may also be used but this rarely confers an advantage.

Thus, the acid chlorides obtained contain practically no catalyst as an impurity.

For some of their uses it will not even be necessary to distil them, and an operation which could be difficult may thus be eliminated.

On the other hand, when a distillation is carried out, it will be very easy to recycle the catalyst from the distillation residue, and this is also highly advantageous. In addition, the new catalysts according to the invention remain active even after several successive phosgenation operations.

The hexasubstituted guanidinium salts which are used are preferably halides and especially hexasubstituted guanidinium chlorides, complexed or otherwise with an acid containing hydrogen and a halogen, preferably hydrochloric acid.

The radicals $R_1$ to $R_6$, defined earlier, may denote, for example, saturated aliphatic radicals containing from 1 to 12 carbon atoms, preferably from 1 to 4 carbon atoms, or unsaturated aliphatic radicals containing from 3 to 12 carbon atoms, preferably from 3 to 8 carbon atoms, saturated or unsaturated alicyclic radicals containing from 5 to 6 carbon atoms, araliphatic radicals containing from 7 to 12 carbon atoms, especially benzyl radicals, and phenyl radicals.

$R_1$ and $R_2$ and/or $R_3$ and $R_4$ and/or $R_5$ and $R_6$ may denote, with the nitrogen atom to which they are attached, for example, a 5- or 6-membered heterocyclic ring which may contain another heteroatom, such as oxygen, such as, for example, the morpholine ring.

$R_1$ and $R_6$ and/or $R_5$ and $R_4$ and/or $R_2$ and $R_3$ may form, with the N-C-N group, a 5- or 6-membered heterocyclic ring, such as in particular the ring

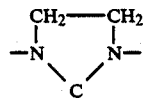

The substituents in radicals $R_1$ to $R_6$ are groups which are inert under the reaction conditions and are chosen, for example, from halogen atoms and alkyl, alkoxy, aryloxy and nitro groups.

Preferably, radicals $R_1$ to $R_6$ denote methyl, ethyl, n-propyl, n-butyl, isopropyl, isobutyl, allyl, cyclohexyl, phenyl, 4-chlorophenyl and benzyl radicals.

The catalysts according to the invention may be prepared in a known manner by a number of methods.

For example, they may be prepared from a urea or thiourea which is phosgenated to produce the chloroformamidinium chloride (Chem. Ber. 97, p. 1232 (1964)) which is then reacted with an amine (Synthesis 1983 (11) 904–905), or by reacting a thiourea with a carbamyl chloride (Liebigs Ann. Chem. 1984, 108–126), or from pentaguanidines which are reacted with a halogen derivative (Houben-Weyl VIII p. 100 and 186, 1952), the pentaguanidines themselves being obtained by reacting an isocyanato dihalide with a secondary amine (French Pat. No. 1,453,438).

The hexasubstituted guanidinium salt complexes may be prepared by the addition of the acid containing hydrogen and a halogen to the hexasubstituted guanidinium salts.

The complex of hexasubstituted guanidinium chloride with hydrochloric acid is prepared, in particular, by the reaction of the chloroformamidinium chloride with a secondary amine followed, without isolation of the products obtained, by a phosgenation.

The reactions are as follows:

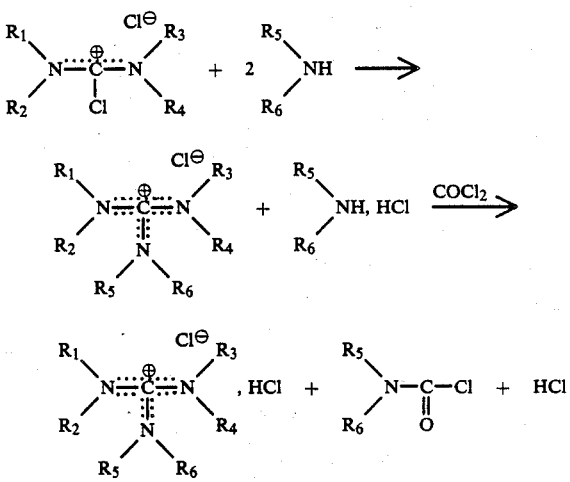

This process is of particular interest because it is unnecessary to use an excess of a base to remove the amine hydrochloride formed in the first stage, since in the second stage this is converted into a carbamyl chloride which can be readily separated by distillation.

The acid chlorides may be obtained according to the invention from most carboxylic acids.

As an example, there may be mentioned the carboxylic acids of formula $R(COOH)_n$ in which $n=1$ or 2 or 3 and R denotes a saturated or otherwise, substituted or otherwise, linear or branched aliphatic radical containing up to 30 carbon atoms, a saturated or otherwise, substituted or otherwise, $C_3$–$C_6$ alicyclic radical, a substituted or otherwise, araliphatic radical, a substituted or otherwise, aromatic radical, or a heterocyclic radical.

As substituents in the radical R there may be mentioned, for example, halogen atoms, especially chlorine, fluorine and bromine, and alkyl or haloalkyl, alkoxy, phenoxy and nitro groups.

The carboxylic acids which are preferred within the scope of the present invention are chosen from the group consisting of acetic acid, propionic acid, butyric acid, 2-ethylexanoic acid, nonanoic acid, stearic acid, benzoic acid, lauric acid, palmitic acid, undecyclenic acid, acrylic acid and methacrylic acid.

The acid phosgenation reaction in the presence of the catalysts of the invention takes place preferably without any solvent.

When the acids have a low boiling point or a high melting point, for example above 100° C., it is possible to use a solvent or a mixture of solvents which are inert towards phosgene and are chosen, for example, from chlorinated aliphatic hydrocarbons such as dichloroethane, and aromatic hydrocarbons such as toluene, xylene, chlorobenzene or dichlorobenzene.

Phosgene is preferably introduced as a gas into the reaction medium, which is heated and maintained at an appropriate temperature.

In most cases it is preferable to use a slight excess of phosgene, generally between 5 and 25%.

It is also possible to operate continuously by introducing phosgene and the acid simultaneously into the reactor and by continuously separating the acid chloride formed.

The reaction is generally carried out at a temperature of between 80° and 160° C. and preferably between 100° and 140° C.

By virtue of the process of the invention acid chlorides are obtained practically free from impurities. The purification operations are simplified and the catalyst may be readily recycled.

Acid chlorides are known compounds which have very many applications. They are particularly useful for the preparation of peresters and peroxides, radical polymerization initiators, and pesticide products.

The following examples illustrate the invention without limiting it in any way.

EXAMPLE 1

Preparation of the complex of hexa-n-butguan,,um chloride and hydrochloride acid

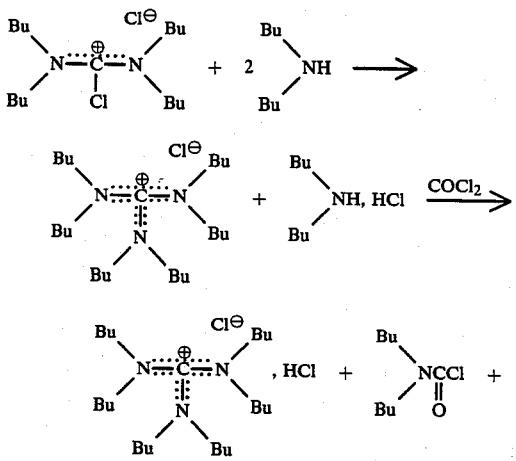

0.06 mole of di-n-butylamine dissolved in 10 ml of toluene is introduced into a reactor which is fitted out.

0.03 mole of tetrabutylchloroformamidinium chloride dissolved in 25 ml of toluene is then added while the temperature is allowed to vary between 30° and 60° C.

The reaction mixture is stirred for half an hour at a temperature in the region of 20° C. and then 0.04 mole of gaseous phosgene is introduced at a temperature in the region of 20° C.

The mixture is heated to 110° C. and then stirred for 2 hours.

After degassing and removal of toluene by evaporating under vacuum, the residue is taken up in ether. 10.5 g (75% yield) of the expected complex are obtained, precipitated in the form of white crystals.

Melting point: 90° C.

Elemental analysis:

|  | C | H | N | Cl |
|---|---|---|---|---|
| Calculated | 64.1 | 11.75 | 8.88 | 15.17 |
| Found | 63.42 | 11.48 | 8.08 | 15.31 |

EXAMPLES 2 TO 17

Preparation of acid chlorides

Various acid chlorides are prepared in accordance with the following operating procedure:

1 mole of carboxylic acid, a variable quantity of catalyst and, if appropriate, the solvent are introduced into a reactor fitted with a stirrer, a thermometer, a dip tube and a reflux condenser cooled to $-70°$ C.

The reaction mixture is heated to the required temperature and approximately 1.2 mole (119 g) of gaseous phosgene is introduced slowly while the temperature is maintained.

When the introduction of phosgene has ended, stirring is continued at the temperature of phosgenation until the remaining acid and the anhydride formed have completely disappeared (1 hour on average).

Excess phosgene is then removed by degassing with nitrogen or under reduced pressure.

The acid chloride obtained is purified by distillation where applicable.

Potentiometric determination of the acid chlorides is carried out by determining the amine hydrochloride formed by the reaction of m-chloroaniline with the acid chloride, using the Siggia Procedure B.226-1979 method.

The acids, the catalysts and the operating conditions employed are collated in the following table, together with the results obtained.

| Ex. No. | Acid | Catalyst | Catalyst/acid, mole % | Total phosgenation time (h) | Temperature °C. | Chloride yield % | Purity* % |
|---|---|---|---|---|---|---|---|
| 2 | Butyric | $\{Bu_2N\text{—}C^\oplus Cl^\ominus\}_3$ | 0.1 | 6 | 125-102 | distilled 90 | 98.7 |
| 3 | 2-Ethylhexanoic | $\{Bu_2N\text{—}C^\oplus Cl^\ominus\}_3$ | 0.1 | 1 | 130-140 | distilled 94 | 99 |

-continued

| Ex. No. | Acid | Catalyst | Catalyst/acid, mole % | Total phosgenation time (h) | Temperature °C. | Chloride yield % | Purity* % |
|---|---|---|---|---|---|---|---|
| 4 | 2-Ethylhexanoic | [Bu$_2$N]$_3$C$^⊕$ Cl$^⊖$ | 0.1 | 6 | 80–85 | distilled 93 | 99.5 |
| 5 | 2-Ethylhexanoic | [Bu$_2$N]$_3$C$^⊕$ Cl$^⊖$ | 0.02 | 6 | 120–125 | distilled 94 | 99.7 |
| 6 | 2-Ethylhexanoic | [Bu$_2$N]$_3$C$^⊕$ Cl$^⊖$, HCl | 0.02 | 6 | 120–125 | distilled 93 | 99.9 |
| 7 | 2-Ethylhexanoic | [Me$_2$N]$_2$C$^⊕$—N(Bu)$_2$ Cl$^⊖$ | 0.05 | 3h45 | 120–125 | distilled 93 | 99.9 |
| 8 | Nonanoic | [Me$_2$N]$_2$C$^⊕$—N(CHMe$_2$)(CH$_2$Ph) Cl$^⊖$ | 0.05 | 4h30 | 120–125 | distilled 90 | 100 |
| 9 | Stearic | [Bu$_2$N]$_3$C$^⊕$ Cl$^⊖$ | 0.05 | 2h30 | 130–140 | crude 100 | 99.3 |
| 10 | Stearic | [Bu$_2$N]$_3$C$^⊕$ Cl$^⊖$ | 0.02 | 4 | 120–125 | crude 100 | 100 |
| 11 | Stearic | [Bu$_2$N]$_3$C$^⊕$ Cl$^⊖$, HCl | 0.02 | 4 | 120–125 | crude 100 | 100 |
| 12 | Benzoic | [Bu$_2$N]$_3$C$^⊕$ Cl$^⊖$ | 0.1 | 6 | 120–125 | distilled 93 | 100 |
| 13 | Lauric | [(Bu)$_2$N]$_3$C$^⊕$ Cl$^⊖$, HCl | 0.02 | 7h | 115–120 | distilled 90 | 99 |
| 14 | Palmitic | [(Bu)$_2$N]$_3$C$^⊕$ Cl$^⊖$, HCl | 0.02 | 6h | 115–120 | crude 100 | 98 |
| 15 | Undecylenic | [(Bu)$_2$N]$_3$C$^⊕$ Cl$^⊖$, HCl | 0.1 | 4h | 115–120 | distilled 83 | 98 |
| 16 | Propionic | [(CH$_3$)$_2$N]$_3$C$^⊕$ Cl$^⊖$ | 0.2 | 7h | 80–85 | distilled 94 | 97 |
| 17 | Acrylic | [(CH$_3$)$_2$N]$_3$C$^⊕$ Cl$^⊖$ HCl | 0.5 | 7h | 115–150 | distilled 74 | 99 |

*Chlorine content by potentiometric analysis (%).

What is claimed is:

1. Process for the preparation of carboxylic acid chlorides comprising reacting phosgene with a carboxylic acid in the presence of a catalyst, wherein said catalyst is chosen from the group consisting of hexasubstituted guanidinium salts or their complexes with acids containing hydrogen and a halogen, represented by the following formulae:

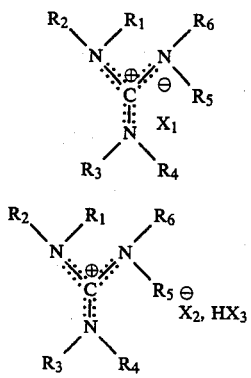

in which $R_1$, $R_2$, $R_3$, $R_4$, $R_5$ and $R_6$, are identical or different and denote:
- saturated or unsaturated linear or branched aliphatic radicals, no unsaturation being situated on the carbons of groups $R_1$ to $R_6$ that adjoin the nitrogen atom;
- saturated or unsaturated alicyclic radicals, no unsaturation being situated on the carbons of groups $R_1$ to $R_6$ that adjoin the nitrogen atom;
- araliphatic radicals;
- aromatic radicals;
- or form, with the nitrogen atom to which they are attached and with the other radical $R_1$ to $R_6$ attached to the same nitrogen atom, a saturated or unsaturated heterocyclic ring, no unsaturation being situated on the carbons of groups $R_1$ to $R_6$ that adjoin the nitrogen atom, and wherein said heterocyclic ring includes from 0 to 1 oxygen atoms;
- or, at least one of the pairs $R_1$ and $R_6$, $R_4$ and $R_5$, and $R_2$ and $R_3$ form, with the nitrogen atoms to which each radical $R_1$ to $R_6$ are attached and the central carbon atom in formulae I and II, saturated or unsaturated heterocyclic ring, no unsaturation being situated on the carbons of groups $R_1$ to $R_6$ that adjoin the nitrogen atom;

$X_1$ denotes an anion chosen from the group consisting of $Cl^-$, $Br^-$, $I^-$, $BF_4^-$, $CN^-$, $ClO_4^-$, $NO_3^-$, $NO_2^-$, $OCN^-$, $CH_3SO_4^-$, and $HSO_4^-$; and $X_2$ and $X_3$, which are identical or different, denote chlorine or bromine atoms.

2. Process according to claim 1, wherein radicals $R_1$ to $R_6$ are saturated aliphatic radicals containing from 1 to 12 carbon atoms; unsaturated aliphatic radicals containing from 3 to 12 carbon atoms; saturated or unsaturated alicyclic radicals containing from 5 to 6 carbon atoms; araliphatic radicals contaning from 7 to 12 carbon atoms; or phenyl radicals; or form, with the nitrogen atom to which they are attached and with the other radical $R_1$ to $R_6$ attached to said nitrogen atom, a heterocyclic ring containing 5 to 6 members which includes from 0 to 1 oxygen atoms; or, at least one of the said pairs, form, with said nitrogen atoms to which each radical $R_1$ to $R_2$ are attached and said central carbom atom, a heterocyclic ring containing 5 or 6 members.

3. Process according to claim 1, wherein $R_1$ to $R_6$ are saturated aliphatic radicals containing from 1 to 4 carbon atoms; unsaturated aliphatic radicals containing from 3 to 8 carbon atoms; alicyclic radicals containing from 5 to 6 carbon atoms; or benzyl radicals.

4. Process according to claim 1, wherein the radicals $R_1$ to $R_6$ are substituted with at least one group or atom selected from the class consisting of halogen atoms and alkyl, alkoxy, aryloxy and nitro groups.

5. Process according to claim 1, wherein $X_1$ is a chlorine or bromine atom and $X_2$ and $X_3$ denote chlorine atoms.

6. Process according to claim 1, wherein said catalyst is used in a quantity of between $10^{-4}$ and $5 \times 10^{-3}$ equivalent per equivalent of acid.

7. Process according to claim 1, wherein an excess of phosgene of between 5 and 25% is used.

8. Process according to claim 1, wherein said process is carried at a temperature between 80° and 160° C.

9. Process according to claim 1, wherein said process is carried out in a solvent or a mixture of solvents which are inert towards phosgene and are chosen from the group consisting of chlorinated aliphatic hydrocarbons and aromatic hydrocarbons.

10. Process according to claim 1, wherein said carboxylic acid is an acid of formula $R(COOH)_n$ in which $n=1$, 2 or 3, and R denotes:
- a saturated or unsaturated, substituted or unsubstituted, linear or branched aliphatic radical containing up to 30 carbon atoms;
- substituted or unsubstituted $C_3$–$C_6$ alicyclic radical;
- a substituted or unsubstituted araliphatic radical;
- a substituted or unsubstituted aromatic radical; or a heterocyclic radical;
- wherein when R is substituted, the substituents comprise at least one group or atom selected from halogen atoms and alkyl, haloalkyl, alkoxy, phenoxy, and nitro groups.

11. Process according to claim 7, wherein said process is carried out continuously by simultaneous introduction of said carboxylic acid and phosgene.

12. Process according to claim 6, wherein said catalyst is used in a quantity of between $10^{-4}$ and $10^{-3}$ equivalent per equivalent of acid.

13. Process according to claim 8, wherein said process is carried at a temperature between 100° and 140° C.

* * * * *